United States Patent [19]

Bukkems et al.

[11] Patent Number: 4,494,413
[45] Date of Patent: Jan. 22, 1985

[54] HOMOGENEOUS SAMPLER FOR NON-HOMOGENEOUS FLOWING OF FLUID

[75] Inventors: Franciscus H. J. Bukkems, The Hague; Arnon Plaschkes; Cornelis Buurman, both of Amsterdam; Anton M. P. Broere, The Hague, all of Netherlands

[73] Assignee: Shell Oil Company, Houston, Tex.

[21] Appl. No.: 414,084

[22] Filed: Sep. 2, 1982

[30] Foreign Application Priority Data

Sep. 30, 1981 [GB] United Kingdom ............... 8129572

[51] Int. Cl.³ .......................... G01N 1/20; G01N 1/18
[52] U.S. Cl. ............... 73/863.43; 73/863.52; 73/863.58; 366/137; 366/140
[58] Field of Search .......... 73/863.86, 863.43, 863.03, 73/863.02, 863.58, 863.61, 863.52; 366/140, 136, 137

[56] References Cited

U.S. PATENT DOCUMENTS

| | | | |
|---|---|---|---|
| 1,438,733 | 12/1922 | Werner | 366/137 |
| 1,445,427 | 2/1923 | Werner | 366/137 |
| 1,737,704 | 12/1929 | Bond | 366/137 |
| 1,992,261 | 2/1935 | Traudt | 366/137 X |
| 2,322,018 | 6/1943 | Huber | 73/863.61 X |
| 2,437,694 | 3/1948 | Hickman | 366/137 X |
| 3,086,538 | 4/1963 | Voltz | 366/137 X |
| 3,271,304 | 9/1966 | Valdespino et al. | 366/137 X |
| 3,282,113 | 11/1966 | Suchnik | 73/864 X |
| 3,930,414 | 1/1976 | Russel | 73/863.86 X |
| 3,940,993 | 3/1976 | Lapidot | 73/863.02 |
| 3,950,136 | 4/1976 | Bellinja | 73/863.02 |
| 4,091,835 | 5/1978 | Frampton | 73/863.03 X |
| 4,167,117 | 9/1979 | Stokley et al. | 73/863.58 |
| 4,299,501 | 11/1981 | Patil et al. | 366/136 X |
| 4,307,620 | 12/1981 | Jiskoot | 73/863.61 X |
| 4,328,710 | 5/1982 | Cymbalisty et al. | 73/863.86 |
| 4,403,517 | 9/1983 | Thomte | 73/863.43 X |
| 4,426,880 | 1/1984 | Walters et al. | 73/863.43 X |

FOREIGN PATENT DOCUMENTS 1050087 2/1959 Fed. Rep. of Germany ... 73/863.86
1142557 9/1957 France .................................. 366/137

Primary Examiner—Stephen A. Kreitman
Assistant Examiner—Tom Noland

[57] ABSTRACT

A process and apparatus are provided for continuously sampling, for example, crude oil, to determine the amount of water and bottom sediments in the crude oil, wherein the crude oil is passed through a mixing zone in a pipeline to homogenize the crude oil, a fluid stream is continuously withdrawn from the homogenized crude oil and introduced into a collecting vessel. The collected fluid is mixed for homogenization, whereafter a sample is taken from the fluid for analysis.

6 Claims, 2 Drawing Figures

HOMOGENEOUS SAMPLER FOR NON-HOMOGENEOUS FLOWING OF FLUID

BACKGROUND OF THE INVENTION

For various reasons it may be necessary to take representative samples of non-homogeneous fluids in order to determine the concentration of the components in the fluids. The sampling of a fluid is normally combined with the transport of the fluid through a pipeline, being one of the most important transporting means in many industries handling large quantities of fluids.

One example where the sampling of fluids has become increasingly important in the recent years is found in the oil industry. Sampling of crude oil for determining the net amount of oil has to be performed very accurately in connection with the metering of crude oil for royalty purposes. The knowledge of the correct amount of hydrocarbons in the available crude oil will further enable refinery operation management to draw up more accurate mass balances, so that the various refinery operations may be carried out in the most efficient manner.

A large variety of methods are known for sampling fluids; however, all these methods suffer from being not accurate enough when non-homogeneous fluids are to be sampled. The main reason for this inaccuracy consists herein that the samples which are taken from a fluid stream in a pipeline in the known methods are not representative for the bulk of fluid but only for that part of the fluid passing the sample point at the moment the samples are taken.

A problem in sampling crude oil to determine the content of water and bottom sediments in the oil, is formed by the fact that the water and other contaminations are hardly ever uniformly distributed in the oil. When crude oil is stored in a tank, the water and bottom sediments will settle down in the bottom part of the tank. When, for example, crude oil is unloaded from a tanker and transferred through a pipeline the amount of water and bottom sediments in the crude oil will exhibit large fluctuations. When the unloading of a tank in the tanker is in an advanced stage the crude oil passing through the pipeline will contain no or only small amounts of water dispersed therein. However, when the unloading of a further tank is started the amount of water in the crude oil will suddenly increase, and even slugs of water ray pass through the pipeline. Samples taken from the first part of the crude oil unloaded from a tanker may therefore totally differ from samples taken from the crude oil during the last part of the unloading. None of these samples nor the combined samples will necessarily be representative for the total mass of crude oil unloaded from the tanker. Further large variations in throughput may occur during the unloading process, causing further inaccuracies in the known sampling methods.

SUMMARY OF THE INVENTION

The primary purpose of the present invention is to provide a process and an apparatus for sampling a mass of a non-homogeneous fluid, which are more accurate than the known processes and apparatuses. The process for sampling a mass of a non-homogeneous fluid according to the invention thereto involves the steps of:
  a. passing the mass of the non-homogeneous fluid through a pipeline as a fluid stream;
  b. passing the fluid stream through a mixing zone in the pipeline under conditions of turbulent flow;
  c. continuously withdrawing a part of the mixed fluid stream adjacent to the mixing zone at a velocity substantially equal to the velocity of the fluid stream in the pipeline;
  d. introducing the withdrawn fluid stream part into a collecting vessel;
  e. agitating the withdrawn fluid stream part collected in the collecting vessel; and
  f. withdrawing a sample from the agitated withdrawn fluid stream part for analysis.

The apparatus for sampling a mass of a non-homogeneous fluid involves according to the invention a pipeline provided with a first mixing device forming a mixing zone in the pipeline, an open-ended conduit having one end arranged in the pipeline adjacent to the downstream end of the mixing device and the other end connected to a collecting vessel, said collecting vessel being provided with a second mixing device, and means for taking a sample from the collecting vessel.

In the process according to the invention a sample is obtained which is representative for the whole mass of a non-homogeneous fluid passed through a pipeline since continuously a certain part of the fluid flowing through a pipeline is withdrawn after homogenization and used to prepare a final sample.

DESCRIPTION OF THE DRAWINGS

The invention will hereinafter be described by way of example in more detail with reference to the accompanying drawings, wherein.

CDESCRIPTION OF PREFERRED EMBODIMENTS

Figure 1:
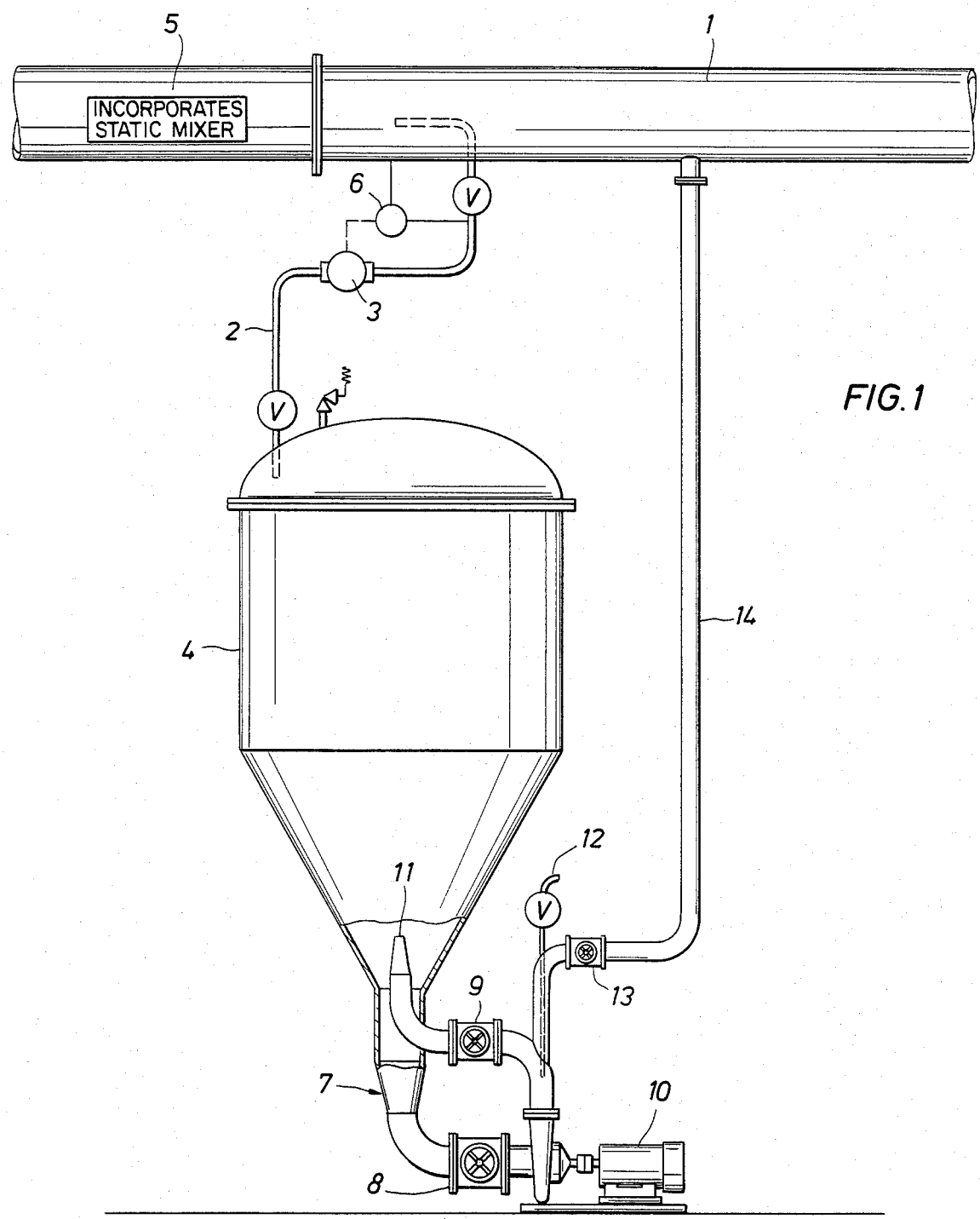
FIG. 1 shows a first embodiment of the invention.

FIG. 1 shows a transfer pipeline 1 for the transfer of crude oil or another fluid, from a first tank (not shown) of, for example, a crude oil tanker to a second tank (not shown), for example a land storage tank. For analyzing the composition of the crude oil unloaded from said first tank a small stream of crude oil is continuously withdrawn from the main stream in the transfer pipeline 1, via a conduit 2 provided with a pump 3 and collected in a collecting vessel 4. During the transfer of crude oil through the transfer pipeline 1, water and bottom sediments are segregated from the oil and tend to flow in the bottom part of the transfer pipeline due to the differences in specific gravity of the various components. As a consequence thereof there may be large concentration differences in the crude oil over the pipeline cross section. To guarantee that the fluid withdrawn via conduit 2 is representative for the crude oil passing through the transfer pipeline 1, two main requirements have to be fulfilled. Firstly, the crude oil must be homogenized prior to reaching the cross section of transfer pipeline 1 where the inlet of conduit 2 is arranged. To this end a so-called static mixer 5, comprising a pipe segment internally provided with not separately shown fixedly mounted, inclined vanes, is arranged in the pipeline 1 adjacent to the inlet of the conduit 2. Upon passing the static mixer 5 a whirling motion is imparted to the crude oil, causing a homogenization of the crude oil over the cross section of the transfer pipeline 1. Secondly, a part of the homogenized crude oil must be withdrawn via conduit 2 at a velocity substantially equal to the flow velocity in the transfer pipeline 1. A lower velocity in the conduit 2 than in the transfer pipeline 1 would give a too high water concentration in the withdrawn fluid stream because of the inertia of the relatively dense water droplets. A higher velocity in the conduit 2 than in the transfer pipeline 1 would result in a too low water concentration in the withdrawn fluid stream. To prevent any inaccuracies in the sampling as a result of flow fluctuations in the main stream in transfer pipeline 1 a flow rate controller 6 is arranged for controlling the pump speed of the pump 3. To prevent adverse effects of the wall of transfer pipeline 1 and the vanes of the static mixer 5, positions of the inlet of conduit 2 close to said wall and in the wake of the vanes should be avoided. The inlet part of the conduit 2 points in the direction of the fluid flow in the transfer pipeline 1, whereas the inlet end of said conduit 2 is provided with a sharp edge to introduce fluid in the conduit 2 as regularly as possible.

The withdrawn fluid stream is collected in the collecting vessel 4. After completion of the oil transfer operation through the pipeline 1, and introduction of the whole withdrawn fluid stream into collecting vessel 4, the fluid in the vessel 4 is homogenized prior to taking a sample from the content of the vessel 4. In order to homogenize said fluid, a recycling system consisting of a return loop 7 provided with valves 8 and 9 and a recycling pump 10 is arranged at the lower end of the collecting vessel 4. Said return loop 7 has a nozzle-shaped outlet end 11 centrally arranged in the bottom portion of the collecting vessel 4. When valves 8 and 9 are open fluid from the collecting vessel 4 is passed by means of the recycling pump 10 via return loop 7 back into the collecting vessel 4 through the nozzle-shaped outlet end 11 as a high velocity fluid jet. The fluid jet causes turbulence of the fluid in the collecting vessel 4, resulting in a homogenization of the fluid. The collecting vessel 4 may be made suitable for collecting and homogenizing of small quantities of fluid by the arrangement of a roof (not shown) floating on the fluid in the collecting vessel 4. When the fluid has been sufficiently mixed, a sample of the mixed fluid is discharged via a sample line 12. The inlet of said sample line 12 is preferably arranged adjacent to the outlet of the recycling pump 10, so that the turbulence obtained by passing the said pump 10 supports the homogenization of the fluid passing the sample line 12. By closing valve 9 in the downstream part of the return loop 7 and opening a valve 13 in a return pipeline 14, the fluid from the collecting vessel 4 is recirculated to the part of the transfer pipeline 1 positioned downstream of the conduit 2.

By analyzing the sample from the sample line 12 for example by means of distillation or centrifugation, the amount of contaminants, i.e. mainly water and bottom sediments in the total mass of crude oil unloaded from a tank and passed through the transfer pipeline 1 can be determined.

Figure 2:
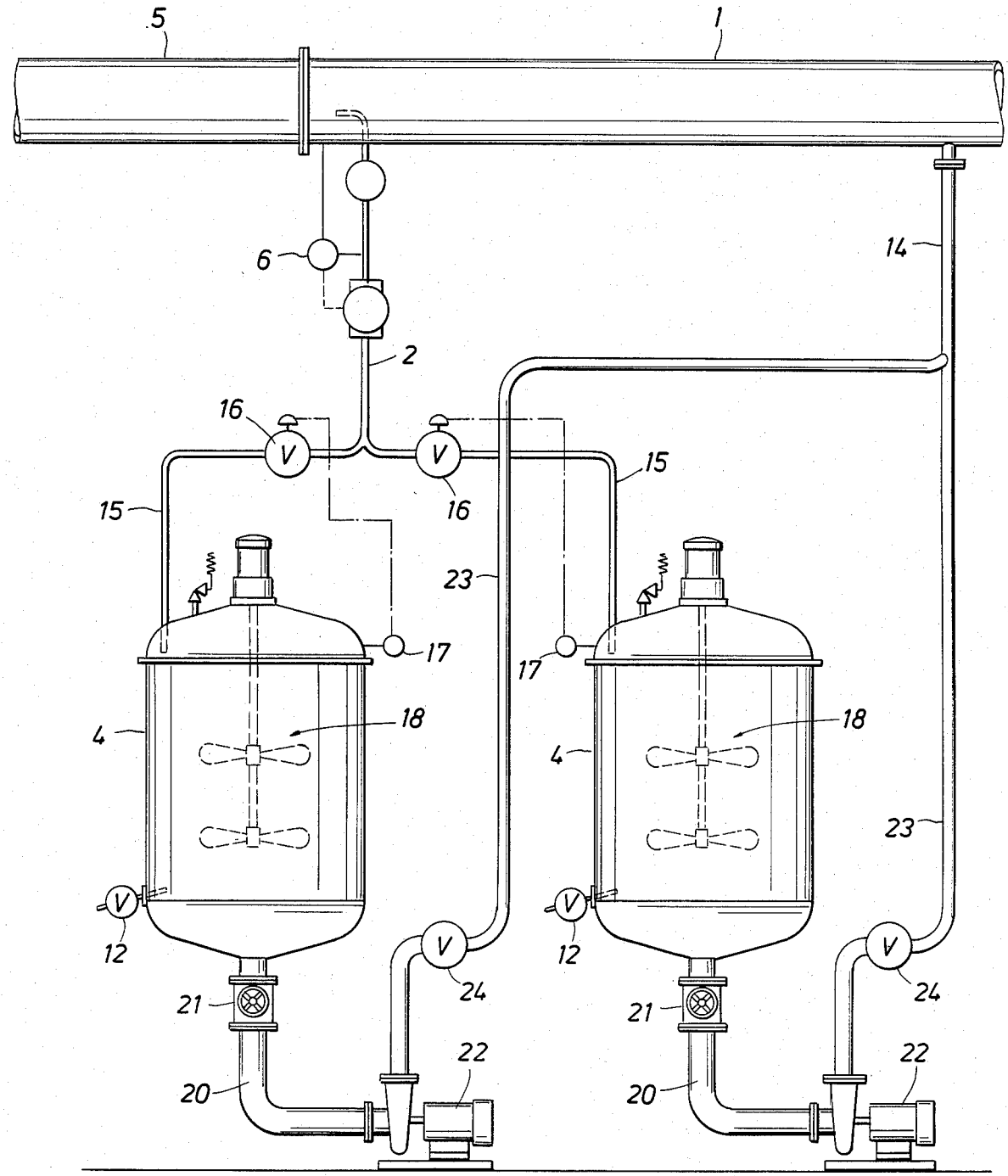
FIG. 2 shows a second embodiment of the invention.

Reference is now made to FIG. 2 showing a second embodiment to the invention.

The apparatus for taking samples from fluids shown in FIG. 2 comprises two collecting vessels 4, which may be brought into fluid communication with the transfer pipeline 1 via branches 15 of conduit 2. Said branches are each provided with a valve 16, being connected to a level controller 17 of a collecting vessel 4. The collecting vessels 4 are each provided with a mixing device 18 comprising a plurality of rotatable blades, forming an alternative to the recycling system shown in FIG. 1. An outlet conduit 20 provided with a valve 21 is arranged at the bottom part of each collecting vessel 4, for transferring fluid by means of a pump 22 from a collecting vessel 4 to branches 23 provided with valves 24, of return pipeline 14. When the apparatus shown in FIG. 2 is in operation for sampling a mass of a non-homogeneous fluid being passed through the transfer pipeline 1, the collecting vessels 4 are alternately filled with fluid withdrawn from the transfer pipeline 1 via conduit 2. When the fluid has reached the maximum level in a collecting vessel 4, valve 16 in the relevant branch 15 is closed and the fluid from conduit 2 is transferred to the other collecting vessel 4 by opening the accompanying valve 16.

In the meantime the fluid in the filled collecting vessel is agitated by rotating the blades 19 of fixing device 18 until the contaminations in the fluid have been equally distributed over the whole mass of fluid. A sample is subsequently taken from the homogenized fluid via sample line 12, whereafter the contents of the collecting vessel 4 is returned to transfer pipeline 1 via outlet conduit 20 and return pipeline 14 by opening valve 21 and actuating pump 22. A fluid sample is taken from the discharged fluid via sample line 12. The procedure of filling and sampling is repeated until the whole mass of fluid to be sampled has passed the rixing zone formed by static mixer 5 and the cross section of the transfer pipeline 1, where the inlet of conduit 2 is positioned. In the system as shown in FIG. 2 a plurality of samples are obtained which may be analyzed separately or as a whole for determining the composition of the mass of fluid passed through the transfer pipeline 1.

It will be understood that the collecting vessels 4 used in the system of FIG. 2 may be relatively small-sized compared with the single collecting vessel 4 in the system shown in FIG. 1. In the sampling apparatus shown in the Figures, conduit 2 should preferably have a diameter of 5 through 10 times the maximum droplet diameter of the fluid to be sampled, in order to avoid obstruction of the fluid flow by the wall of said conduit 2. Further, the diameter of the conduit 2 should be chosen so that preferably a turbulent flow of fluid in said conduit is possible, in order to suppress coalescence phenomena, which might occur with a laminar flow.

Although the application of a static mixer for homogenizing the fluid in the transfer pipeline 1 is preferred, any other means, such as a return loop, for agitating the fluid to form a homogeneous mass, may be applied in the process of the invention. Even the pumping means for transferring the fluid through the transfer pipeline 1 can cause sufficient agitation of the fluid. Although a single conduit 2 for withdrawing fluid from the transfer pipeline 1 has been shown in the Figures, it is also possible to apply a plurality of such conduits 2. Due to fluctuations in the flow velocities in the transfer pipeline, it may sometimes occur that the flow velocity is too low for creating a sufficient agitation of the fluid upon passing the mixing zone having a variable cross-sectional area. This may be, for example, obtained by applying a mixing zone consisting of a plurality of mixing devices, such as static mixers, and means for blanking off part of said fixing devices when the flow velocity in the transfer pipeline decreases. Finally, it is noted that instead of one or two collecting vessels 4 as shown in the Figures, any other number of collecting vessels may be applied in the above-described sampling of non-homogeneous fluids.

What is claimed is:

1. A process for sampling a mass of non-homogeneous fluid comprising:
   passing a mass of the non-homogeneous fluid through a pipeline as a fluid stream;
   passing the fluid stream through a mixing zone in the pipeline under conditions of turbulent flow;
   continuously withdrawing a part of the mixed fluid stream adjacent to the mixing zone at a velocity substantially equal to the velocity of the fluid stream in the pipeline;
   introducing the withdrawn fluid stream part into a collecting vessel;
   agitating the withdrawn fluid stream part collected in the collecting vessel by continuously removing fluid from the collecting vessel and jetting the removed fluid via a loop and nozzle back into the fluid in the collecting vessel at a high velocity, the removed fluid exiting the vessel closely adjacent to the nozzle; and
   withdrawing a sample from the agitated withdrawn fluid stream part for analysis from the loop.

2. The process of claim 1, wherein the nozzle is centrally located within the vessel exit part of the loop and pointing into the collecting vessel.

3. The process of claim 2, wherein the nozzle is pointing upwardly from the bottom of the collecting vessel.

4. An apparatus for sampling a mass of non-homgeneous fluid comprising:
   a pipeline provided with a first mixing device forming a mixing zone in the pipeline;
   an open-ended conduit having one end arranged in the pipeline adjacent to the downstream end of the mixing device and the other end connected to a collecting vessel, said collecting vessel being provided with a second mixing device formed by a return loop including a pump to withdraw fluid from the collecting vessel and return it to the collecting vessel as a jet;
   a nozzle centrally located within the vessel exit part of the return loop and pointing into the collecting vessel and operative to form the jet; and
   means for taking a sample from the loop connected to the collecting vessel.

5. The apparatus as claimed in claim 4, further comprising a return pipeline forming a fluid communication between the collecting vessel and the part of the pipeline arranged downstream of the open-ended conduit.

6. The apparatus as claimed in claim 4, wherein the nozzle is pointing upwardly from the bottom of the collecting vessel.

* * * * *